(12) United States Patent
Mansell (10) Patent No.: US 11,351,375 B2
(45) Date of Patent: Jun. 7, 2022

(54) SPINAL CORD STIMULATOR

(71) Applicant: John Mansell, Gillette, WY (US)

(72) Inventor: John Mansell, Gillette, WY (US)

( * ) Notice: Subject to any disclaimer, the term of this patent is extended or adjusted under 35 U.S.C. 154(b) by 90 days.

(21) Appl. No.: 16/490,572

(22) PCT Filed: Mar. 2, 2018

(86) PCT No.: PCT/US2018/020759
§ 371 (c)(1),
(2) Date: Sep. 2, 2019

(87) PCT Pub. No.: WO2018/161029
PCT Pub. Date: Sep. 7, 2018

(65) Prior Publication Data
US 2020/0009386 A1    Jan. 9, 2020

Related U.S. Application Data

(60) Provisional application No. 62/532,464, filed on Jul. 14, 2017, provisional application No. 62/466,487, filed on Mar. 3, 2017.

(51) Int. Cl.
*A61N 1/36* (2006.01)
*A61N 1/05* (2006.01)
(Continued)

(52) U.S. Cl.
CPC ............ *A61N 1/36071* (2013.01); *A61B 8/12* (2013.01); *A61N 1/0551* (2013.01);
(Continued)

(58) Field of Classification Search
CPC .............. A61N 1/36062; A61N 1/0551; A61N 1/3615; A61N 1/36171; A61N 1/36175;
(Continued)

(56) References Cited

U.S. PATENT DOCUMENTS 5,643,330 A   7/1997   Holsheimer et al.
8,452,417 B2  5/2013   Navarro
(Continued)

OTHER PUBLICATIONS

Filing Receipt and Specification for patent application entitled "Electrotherpeutic Modalities Comprising a Phasic Relationship of Electrodes," by John Mansell, filed Jul. 14, 2017 as U.S. Appl. No. 62/532,464.

(Continued)

*Primary Examiner* — Paula J Stice
(74) *Attorney, Agent, or Firm* — Barnes & Thornburg LLP; Jerry C. Harris, Jr.

(57) ABSTRACT

Embodiments of the disclosure include systems and method for spinal cord stimulation. A spinal cord stimulator may comprise a pulse generator comprising electronic circuitry configured to generate output current; at least one lead in communication with the generator and configured to extend into the epidural space of a patient's spinal column; at least one electrode contact located proximate to a distal end of the at least one lead and configured to provide electric stimulation to a portion of a patient's spinal cord; and at least one sensor located along the at least one lead configured to determine a distance between the at least one lead and a surface of the patient's spinal cord, wherein the generator receives the determined distance, and wherein the generator is configured to adjust the stimulation provided by the at least one electrode contact based on the determined distance.

18 Claims, 6 Drawing Sheets

(51) Int. Cl.
*A61N 1/365* (2006.01)
*A61B 8/12* (2006.01)

(52) U.S. Cl.
CPC ....... *A61N 1/3615* (2013.01); *A61N 1/36062* (2017.08); *A61N 1/36171* (2013.01); *A61N 1/36175* (2013.01); *A61N 1/36528* (2013.01); *A61N 1/36535* (2013.01)

(58) Field of Classification Search
CPC . A61N 1/36528; A61N 1/36535; A61N 1/086
See application file for complete search history.

(56) References Cited

U.S. PATENT DOCUMENTS

| | | |
|---|---|---|
| 2004/0236388 A1 | 11/2004 | Gielen et al. |
| 2006/0247732 A1* | 11/2006 | Wesselink ............. A61B 5/1118 607/46 |
| 2007/0168008 A1* | 7/2007 | Olsen ................... A61N 1/0551 607/117 |
| 2008/0033497 A1* | 2/2008 | Bulkes .................... A61N 1/05 607/9 |
| 2013/0241573 A1 | 9/2013 | Gupta et al. |
| 2014/0276925 A1 | 9/2014 | Alves et al. |
| 2015/0360031 A1* | 12/2015 | Bornzin ............. A61N 1/36071 607/62 |

OTHER PUBLICATIONS

Filing Receipt and Specification for patent application entitled "Spinal Cord Stimulator," by John Mansell, filed Mar. 3, 2017 as U.S. Appl. No. 62/466,487.

Foreign communication from a related counterpart application—International Preliminary Report on Patentability, PCT/US2018/020759 dated Sep. 12, 2019, 8 pages.

Foreign communication from a related counterpart application—International Search Report and Written Opinion, PCT/US2018/020759 dated Jun. 15, 2018, 11 pages.

European Patent Office, Supplemental European Search Report issued in EP Application 18761640.4, dated Oct. 29, 2020, 8 pages.

* cited by examiner

SPINAL CORD STIMULATOR

CROSS-REFERENCE TO RELATED APPLICATIONS

This application is a filing under 35 U.S.C. 371 of International Application No. PCT/US2018/020759 filed Mar. 2, 2018, which is a continuation of and claims priority to U.S. Provisional Application No. 62/466,487 entitled "Spinal Cord Stimulator", filed Mar. 3, 2017, and U.S. Provisional Application No. 62/532,464 entitled "Electrotherapeutic Modalities Comprising a Phasic Relationship of Electrodes", filed Jul. 14, 2017, which are incorporated herein by reference.

FIELD

The present disclosure relates generally to medical devices. More particularly, the present disclosure relates to improved methods and devices for electrotherapeutic stimulation such as with spinal cord stimulators and cardiac pacemakers.

BACKGROUND

For over 50 years electrical stimulation of the dorsal column has been utilized as a therapy for the treatment of chronic pain. Generally, a therapeutic intervention with the central, peripheral or autonomic nervous system for therapeutic effect by means of targeted electrical stimulation or pharmacological delivery from implanted devices is termed neuromodulation. Dorsal column stimulation, also termed spinal cord stimulation (SCS), is one of the most established forms of neuromodulation used to treat neuropathic pain. Neuropathic pain refers to pain that is generated by nervous tissue and is a maladaptive response to nerve injury of either the peripheral or central nervous system. Neuropathic pain may exist independently of any form of tissue injury outside of the central nervous system. Examples of conditions that may lead to neuropathic pain include disease (e.g., HIV, Herpes, Diabetes, Cancer, autoimmune disorders), acute trauma (surgery, injury, electric shock), and chronic trauma (repetitive motion disorders, chemical toxicity such as alcohol, chemotherapy, or heavy metals).

SCS is also used to treat ischemic pain syndromes such as chronic critical limb ischemia, angina pectoris and other visceral pain syndromes including chronic pancreatitis, chronic painful bladder syndrome, chronic abdominal pain, brachial plexus injuries, phantom limb pain and ischemic limb pain.

One challenge to the efficacy of SCS as a method of pain management is the observation that SCS voltage and current thresholds have been observed to change with body position. A significant alteration in voltage or current requirements when moving from supine to sitting or standing positions has been noted. Thus, an ongoing need exists to develop SCS systems able to dynamically adapt to alterations in postural positions. Additionally there is a need for methodologies capable of expanding the therapeutic efficacy of SCS to the treatment of visceral pain as well as somatic pain.

SUMMARY

In an embodiment of the disclosure, a spinal cord stimulator may comprise a pulse generator comprising electronic circuitry configured to generate output current; at least one lead in communication with the generator and configured to extend into the epidural space of a patient's spinal column; at least one electrode contact located proximate to a distal end of the at least one lead and configured to provide electric stimulation to a portion of a patient's spinal cord; and at least one sensor located along the at least one lead configured to determine a distance between the at least one lead and a surface of the patient's spinal cord, wherein the generator receives the determined distance, and wherein the generator is configured to adjust the stimulation provided by the at least one electrode contact based on the determined distance.

In another embodiment of the disclosure, a method of electrotherapeutic modality may comprise placing one or more leads within the epidural space of a patient's spinal column; positioning the one or more leads proximate to a target stimulation area of a patient's spinal cord; stimulating at least one electrode contact located proximate to a distal end of the one or more leads by generating an output current by a generator in communication with the one or more leads; determining a distance, by a sensor, between the one or more leads and a surface of the patient's spinal cord; and adjusting a stimulation of the at least one electrode contact based on the determined distance.

In yet another embodiment of the disclosure, a method of electrotherapeutic modality may comprise placing one or more leads within an epidural space of a patient's spinal column; positioning the one or more leads proximate to a target stimulation area of a patient's spinal cord; stimulating a first electrode contact located proximate to a distal end of the one or more leads by generating a first output current by a generator in communication with the one or more leads; stimulating a second electrode contact located proximate to a distal end of the one or more leads by generating a second output current by the generator in communication with the one or more leads; creating a zone of induced current causing stimulation based on stimulating the first electrode contact and the second electrode contact; determining a distance, by a sensor, between the one or more leads and a surface of the patient's spinal cord; and adjusting a position of the zone of induced current causing stimulation based on the determined distance.

DETAILED DESCRIPTION

Disclosed herein are electrotherapeutic modalities comprising a spinal cord stimulation (SCS) system that alters one or more characteristics of the electrical output of the SCS system in response to alterations in the postural characteristics of the subject implanted with the SCS system. In an aspect, the SCS system comprises a plurality of electrodes that can be independently programmed to allow for the delivery of current at a selected time and for a selected duration to address postural changes in a subject being treated, to address visceral pain or both. Hereinafter such systems are referred to as phasic postural altered spinal cord stimulators and designated PACS.

Unless defined otherwise, technical and scientific terms used herein have the same meaning as commonly understood by one of ordinary skill in the art to which the claimed material belongs. The following terms are defined below.

As used herein, the term "in communication" refers to the stimulation lead being adjacent, in the general vicinity, in close proximity, or directly next to or directly on the predetermined stimulation site. Thus, it is to be understand that the lead is "in communication" with the predetermined site if the stimulation results in a modulation of neuronal activity. The predetermined site may be selected from the group consisting of the spinal cord and the dorsal column of the spinal cord which may include the spinal cord area corresponding to cervical vertebral segments C1 to C8, thoracic vertebral segments T1 to T12, or lumbar vertebral segments L1 and L2. Further it is to understand that the spinal cord normally terminates at or just above the second lumbar vertebrae L2. However, in certain subjects the spinal cord may terminate before or after the L2 vertebrae segment, and the claimed material is intended for use along the entire length of the spinal cord regardless of length.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. It is to be understood that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

As used herein, the use of the term "dorsal column" refers to conducting pathways in the spinal cord that are located in the dorsal portion of the spinal cord within the posterior horns and which comprise afferent somatosensory neurons. The dorsal column is also known as the posterior funiculus. Deeper portions of the dorsal horn contain afferent neurons for visceral organs.

As used herein, "epidural space" or "spinal epidural space" refers to an area in the interval between the pia mater or outer lining of the intrathecal space and the bony wall of the spinal canal.

As used herein, the term "neuronal" refers to a neuron which is a morphologic and functional unit of the brain, spinal column, and peripheral nerves.

As used herein, the term "somatosensory system" refers to the peripheral nervous system division comprising primarily afferent somatic sensory neurons and afferent visceral sensory neurons that receive sensory information from skin and deep tissue, including the 12 cranial and 21 spinal nerves.

As used herein, the term "stimulate" or "stimulation" refers to electrical, chemical, heat, and/or magnetic stimulation that modulates the predetermined sites in the nervous system.

As used herein, the term "treating" and "treatment" refers to modulating certain areas of the spinal cord with electrical stimulation so that the subject has an improvement in the disease, for example, improvements in pain without paresthesia. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. It is to be understood that a treatment may improve the disease condition but may not be a complete cure for the disease.

The term "pain" as used herein refers to an unpleasant sensation. For example, the subject experiences discomfort, distress or suffering. It is known to one skilled in the art that various painful conditions may be classified according to broadly opposing or otherwise useful categories. Examples of opposing categories include; nociceptive pain versus non-nociceptive pain and acute pain versus chronic pain. Examples of other common categories of pain used by those skilled in the art include neuropathic pain and phantom pain.

The term "acute pain" as used herein refers to pain that is transient in nature or lasting less than 1 month. Acute pain is typically associated with an immediate injurious process such as soft tissue damage, infection, or inflammation, and serves the purpose of notifying the animal of the injurious condition, thus allowing for treatment and prevention of further injury.

The term "chronic pain" as used herein refers to pain that lasts longer than 1 month or beyond the resolution of an acute tissue injury or is recurring or is associated with tissue injury and/or chronic diseases that are expected to continue or progress. Examples of chronic diseases that are expected to continue or progress may include cancer, arthritis, inflammatory disease, chronic wounds, cardiovascular accidents, spinal cord disorders, central nervous system disorder or recovery from surgery.

The term "neuropathy" as used herein refers to any condition that adversely affects the normal functioning of the nervous system. Neuropathies can originate anywhere in the central or peripheral nervous system, but only in some cases does this produce neuropathic pain.

The term "phantom pain" as used herein refers to a condition whereby the patient senses pain in a part of the body that is either no longer physically present due to amputation, or is known to be completely insensate due to total peripheral nerve destruction.

In an embodiment of the disclosure the electrode arrays or "leads" will have a piezoelectric or ultrasonic sensor integrated into the surface facing the dorsal surface of the spinal cord to emit an ultrasonic pulse on regular or condition-triggered intervals to determine the distance from the leads to the spinal cord. The directly-measured distance information would be utilized to control the amount of current and the lead configuration of current application for ideal stimulation of the patient's spinal cord.

In another embodiment of the disclosure unique and separate supra-physiologic high frequency signals or currents will be applied to different leads simultaneously to create non-linear zones of induced current deeper in the parenchyma of the spinal cord than could otherwise be comfortably tolerated with current curvilinear electric fields generated with simple anode-cathode single frequency and identically phased currents used in current designs.

In yet another embodiment of the disclosure the insulation material for the leads would be comprised of fiber-optic material that would enable the stimulator generator to send optical information to the lead array to control conductivity in the leads, alter lead configuration or enable other special features of the distal lead array such as additional capacitance, or for the leads themselves to send optical information back to the stimulator generator such as the sensing of a strong magnetic field which could cause the generator to go into a safe mode, protecting the patient from injury.

In yet another embodiment the use of conductive carbon fiber with no magnetic moment would render the lead system insensitive to magnetic fields without the need for expensive shielding.

In another embodiment an intraoperative programming display system would combine the information of previous MRI or other imaging of the patient's spine with intraoperative fluoroscopy and the ultrasonically detected distance from the leads to the spinal cord to display modeled electric fields generated during the placement of the leads to optimize communication within the implantation procedure.

Figure 1:
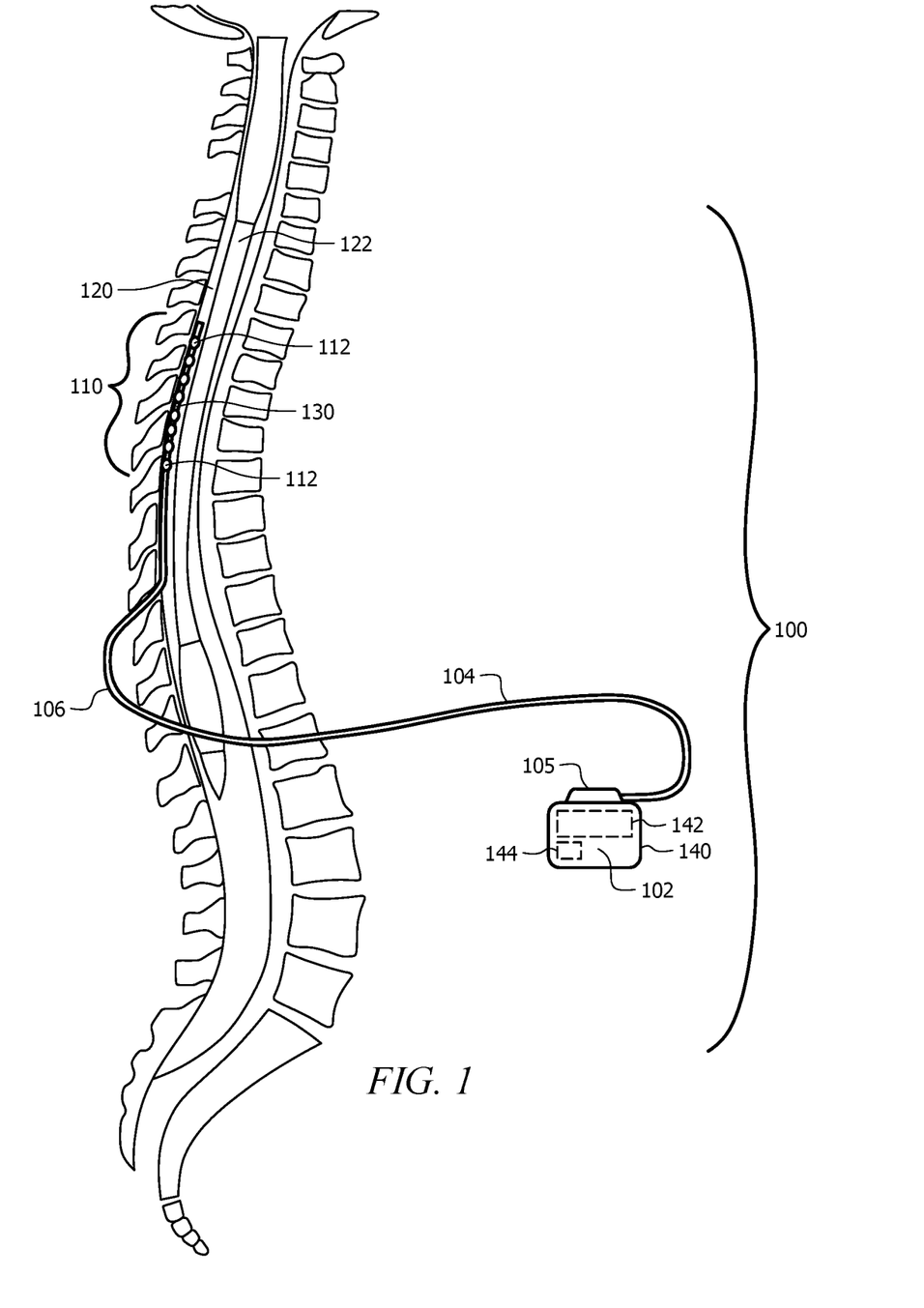
FIG. 1 illustrates an SCS according to an embodiment of the disclosure.

Referring to FIG. 1, spinal cord stimulation, in the simplest form, comprises stimulating electrodes 110 implanted in the epidural space 120, an electrical pulse generator 102 implanted in the lower abdominal area or gluteal region, conducting wires or leads 104 connecting the electrodes 110 to the generator 102, and optionally a generator remote control and a generator charger. FIG. 1 shows a transverse, mid-sagittal view of a spinal cord and a generalized stimulation system 100 that may be used in phasic postural altered spinal cord stimulation (PACS), as well as other stimulation applications.

Such a system 100 may typically comprise an implantable pulse generator (IPG) 102 (which may also be known as an electrical source), a linear or percutaneous stimulation lead 104, and an electrode array 110 that is part of the stimulation lead 104. The electrode array 110 may comprise a plurality of electrode contacts 112. In some embodiments, the electrode contacts 112 can be arranged in an in-line electrode array 110 at the distal end of the lead 104. In some embodiments further described herein, other electrode array configurations can also be used. In operation, the IPG 102 may be configured to generate stimulation current pulses that are applied to selected electrode contacts 112 within the electrode array 110. In some embodiments, the electrode contacts 112 may be individually and selectively controlled to appl the stimulation current pulses. The stimulation lead 104 conducts the stimulation current from the IPG 102 to electrode contacts 112 of the electrode array 110.

The IPG 102 may comprise a header piece or connector block 105 which has at least one opening to accept the connector end of the lead 104 and/or an extension lead or other lead connector. In some cases, the connector block 105 can have two openings to accept the connector ends of two stimulation leads and/or extension leads.

The IPG 102 contains electrical circuitry and can be powered by an internal power source, which through the use of electrical circuitry can output current pulses to each stimulation channel. Communication with the implanted IPG 102 can be accomplished using an external programmer or remote (not shown).

As shown in FIG. 1, at least a portion of the percutaneous stimulation lead 104 and, more particularly, the electrode array 110 are implanted in the epidural space 120 of a patient in close proximity to the spinal cord 122. Because of the lack of space near the lead exit point 106 where the electrode lead 104 exits the spinal column, the IPG 102 may be implanted in the abdomen or above the buttocks.

A power source of the IPG 102 may be connected to the contact or plurality of contacts to enable conduction of electrical impulses to the spinal cord. The spinal cord stimulator lead 106 may contain external contact electrodes 112 at the distal tip, end or on a paddle configure to send impulses into the spinal cord. In an aspect, the distal contact electrodes 112 are independently connected to corresponding contact terminals at the proximal end of the lead 104 by separate stranded wires (lead wires) which run substantially parallel to each other within the lead 104. The proximal conductive terminals may in turn be connected to an electrical power source through a lead extension connector which makes individual contact with the proximal lead terminals and allows transmission of electrical signals from the power source to the distal lead electrodes.

In one embodiment, the electrical source (or IPG) 102 may provide electrical stimulation and allows for the selective and independent variation of characteristics of the electrical power including amplitude, frequency rate, and pulse width, as well as variation in the polarity of the conducting electrode contacts 112 within the lead 104 or plurality of leads 104.

In an embodiment of the present disclosure, the IPG system may comprise an implantable pulse generator 102 and an external portable charger. The IPG 102 may comprise a hermetically sealed case 140 enclosing electronic circuitry 142, including memory circuits, housed within the hermetically sealed case, wherein the electronic circuitry includes a multiplicity of independent bi-directional output current sources, and wherein each output current source is connected to an electrode node. The electronic circuitry 140 may also comprise a multiplicity of coupling capacitors, wherein each coupling capacitor is connected to a respective one of the electrode nodes. The IPG 102 may comprise a header connecter 105 attached to the sealed case 140, the header connecter 105 having a multiplicity of feedthrough pins that pass there-through, wherein each of the multiplicity of coupling capacitors is connected on the sealed side of the case to one of the feedthrough pins. As described above, the IPG 102 may communicate with an electrode array 110 having a multiplicity of electrodes 112 thereon external to said sealed case 140, wherein each electrode 112 is detachably electrically connected to one of the feedthrough pins on a non-sealed side of said sealed case 140, wherein each output current source generates an output stimulus current having a selected amplitude and polarity that, when the output current source is enabled, is directed to the electrode connected thereto through its respective feedthrough pin and coupling capacitor. As described above, the IPG may comprise a signal generator capable of sending an ultrasound-compatible current to the embedded piezoelectric element that measures the distance to the dorsal surface of the spinal cord and circuitry elements capable of sensing the signal and time required for the signal to return and measure the distance to the spinal cord.

In some embodiments, the IPG 102 may comprise a rechargeable battery 144 that provides operating power for the electronic circuitry, a secondary coil, and a rectifier circuit. The IPG system may also comprise a battery charger and protection circuitry that receives externally generated energy through the secondary coil and rectifier circuit, and uses the externally generated energy to charge the rechargeable battery 144. Advantageously, the rectifier circuit may be modulated between a full-wave rectifier circuit and a halfway rectifier circuit, which modulation allows the external portable charger to detect, by monitoring reflected impedance looking into the secondary coil, when the IPG battery has been fully charged.

In the embodiment shown in FIG. 1, the stimulation system 100 may comprise a sensor 130 in communication with the power source and physically part of the linear or paddle electrode array 110. The sensor 130 may be configured to determine the position of the spinal cord 122 with respect to the electrode array 110 and/or lead 104. This sensed position and/or orientation may be used to determine the characteristics of the electrical power, polarity, and activation of the electrode contacts 112 within the electrode array 110. In FIG. 1, the sensor 130 is shown to be positioned near and/or within the electrode array 110, but in other embodiments, the sensor 130 may be located anywhere within the portion of the lead 106 that is within the epidural space 120 of the spinal cord 122.

Figure 2:
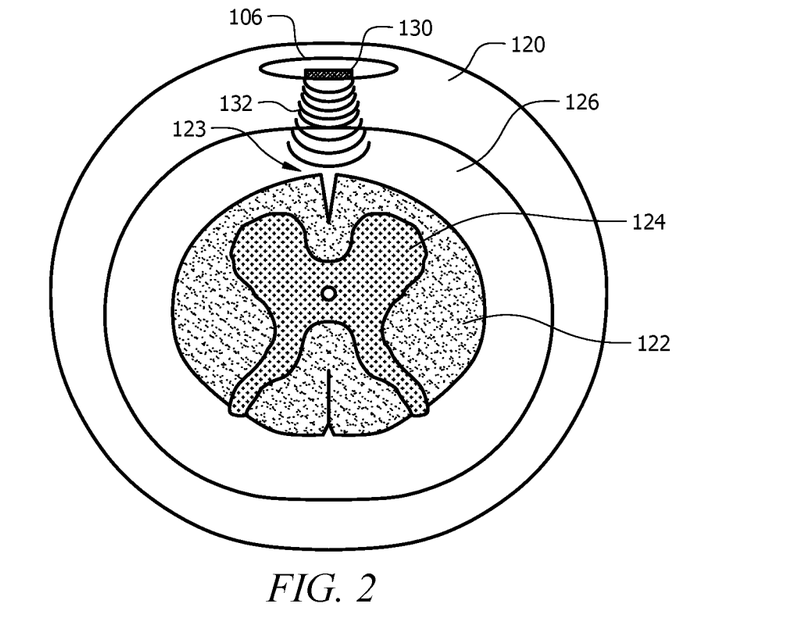
FIG. 2 illustrates a cross-sectional view of an SCS placed within a patient's spinal cord according to an embodiment of the disclosure.

Referring to FIG. 2, the lead 106 is in fluid communication with the sensor 130. The sensor 130 may comprise an ultrasonic sensor, configured to produce and/or detect sound waves 132. In some embodiments, the sensor 130 may comprise a piezoelectric transducer configured to generate the ultrasonic sound waves 132. In some embodiments, the sensor 130 may comprise a receiver configure to detect ultrasonic sounds waves that are reflected back toward the sensor 130 from the spinal cord 122. As shown in FIG. 2, the sensor 130 may be located within the epidural space 120, and may direct sound waves toward a dorsal surface 123 of the spinal cord 122. In the generalized diagram of FIG. 2, the spinal cord 122 may comprise the dorsal horn 124 and may be surrounded by spinal fluid 126. In some embodiments, the lead 104 may be in contact with the spinal lamina, which is a bony structure on each of the spinal vertebrae which provides a roof for the spinal canal and protects the back of the spinal cord.

A PACS 100 of the type disclosed herein accounts for postural changes in a subject having the implanted device by sensing the distance to the dorsal surface 123 of the parenchyma of the spinal cord 122, which is a key variable in stimulation programming of current and lead variable control. In particular, postural changes in a subject having a PACS of the type disclosed herein results in changes in distance to the dorsal surface 123 of the spinal cord 122 detected by the ultrasound sensor 130. The sensor 130 may comprise at least one lead-imbedded piezoelectric sensor and may create an electrical signal to the power source (or IPG) and/or at least one lead that may be configured to adjust the extent and area of electrical stimulation. The adjustment may be determined based on the detected spinal displacement to maintain and/or increase the pain relief associated with the therapy. The combination of the distance information and feedback from the patient drive the details of programming the IPG for effective stimulation with each patient.

Without wishing to be limited by theory, the sensor 130 may comprise at least one piezoelectric transducer, alternatively a plurality of piezoelectric transducers. The sensor 130 may comprise a piezoelectric element configured to produce an ultrasound signal and/or a detector element configured to detect an ultrasound signal. In an embodiment, the ultrasonic sensor 130 of this disclosure is a range sensor that may function by emitting a short burst of ultrasonic sound a suitable frequency from the piezoelectric transducer. In some embodiments, the ultrasonic sensor 130 may generate or emit the ultrasonic sound in response to a postural change of a subject, which may be detected by a motion sensor of some kind (e.g., the IPG and/or another portion of the PACS may comprise a motion sensor). A small amount of sound energy is reflected by the objects (i.e., spinal components) in front of the ultrasonic sensor 130 and returned to the detector of the sensor 130, which may be a piezoelectric transducer. In an embodiment, the ultrasonic sensor 130 further comprises a receiver amplifier which sends these reflected signals (echoes) to a micro-controller, which times them to determine how far away the objects are, by using the speed of sound in the interstitial space and spinal fluid. The calculated range is then converted and used to adjust the pattern and/or amplitude of electrical stimulation in order to provide pain relief In an embodiment of the present disclosure, the information obtained on the calculated range from the ultrasonic sensor 130 may be used to adjust the power and/or configuration of the electrical stimulation in response to postural changes. For example, the information received from the ultrasonic sensor 130 may be utilized to determine a modality for pain relief that may involve stimulation using the distal end a lead or plurality of leads while excluding stimulation from some differing lead or plurality of leads.

Figure 3:
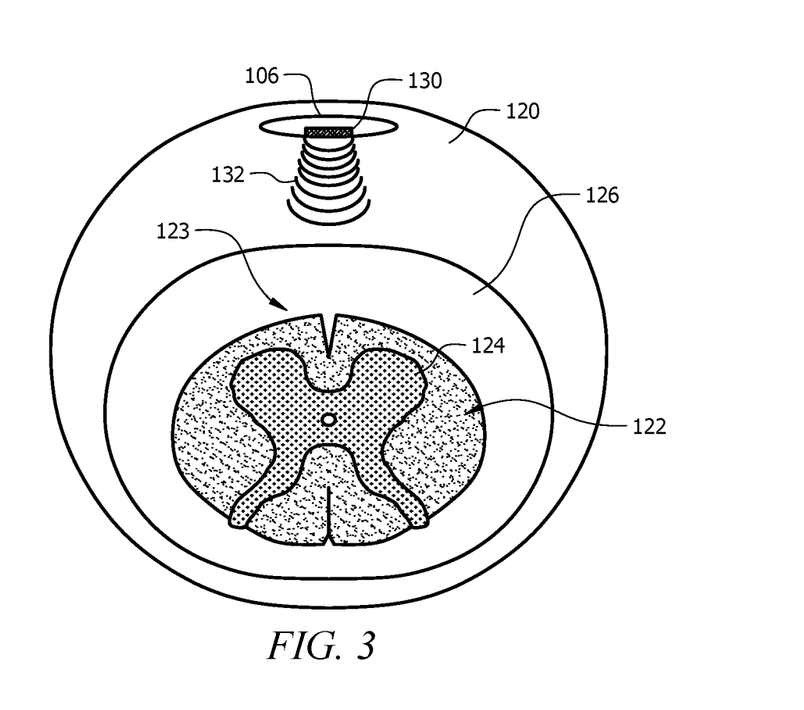
FIG. 3 illustrates another cross-sectional view of an SCS placed within a patient's spinal cord according to an embodiment of the disclosure.

As an example, referring to FIG. 3, a postural change may cause the spinal cord 122 to move within the spinal fluid 126 with respect to the lead 106 and therefore the sensor 130. This change may be detected by determining the distance between the sensor 130 and the dorsal surface 123 of the spinal cord 122 (which is now a greater distance in FIG. 3 than that shown in FIG. 2). The movement of the spinal cord 122, and therefore the dorsal horn 124, may affect the stimulation of the dorsal horn by the lead 106 (i.e., the electrode contacts described in FIG. 1).

In an aspect, the electrical source (or IPG) 102 may comprise a programmable current source which can be used to control the amplitude, phase duration, and phasic relationship of the lead 104 or plurality of leads 104 (and therefore the electrode array 110 and electrode contacts 112). For example, a programmable current source for use in the present disclosure can individually set current, timing, and pulse duration parameters for a lead 104 or a plurality of leads 104 using pulse amplitude controls, pulse timing controls, and pulse duration controls. Hence, each of the electrode contacts 112 can deliver the same strength pulse, for the same time and for the same duration, if desired. Alternatively, the pulse strength, phase, and duration may be each independently be adjusted for each electrode contact 112 relative to one another to generate a phasic relationship of the electrode contacts 112.

In some embodiments, FIG. 2 may illustrate the spinal cord when a patient is laying on their back, wherein during placement of the system 100, the surgeon and/or technician may cycle through a plurality of electrode configurations to establish a target electric field when the spinal cord is in the position shown in FIG. 2. As a part of the process of establishing the target electric field, the sensor 130 may be triggered to determine the current distance between the lead 104 and the dorsal surface of the spinal cord 123, where the target electric field may be associated with this determined distance.

Similarly, FIG. 3 may illustrate the spinal cord when a patient is laying on their stomach. During placement of the system 100, the surgeon and/or technician may cycle through a plurality of electrode configurations to establish a target electric field when the spinal cord is in the position shown in FIG. 3. As a part of the process of establishing the target electric field, the sensor 130 may be triggered to determine the current distance between the lead 104 and the dorsal surface of the spinal cord 123, where the target electric field may be associated with this determined distance, and where this distance and target electric field may be different than those determined as illustrated in FIG. 2.

In some embodiments, a first target electric field may be established when the patient is in a first position (e.g., FIG. 2) and a second target electric field may be established when the patient is in a second position (e.g., FIG. 3).

Figure 4:
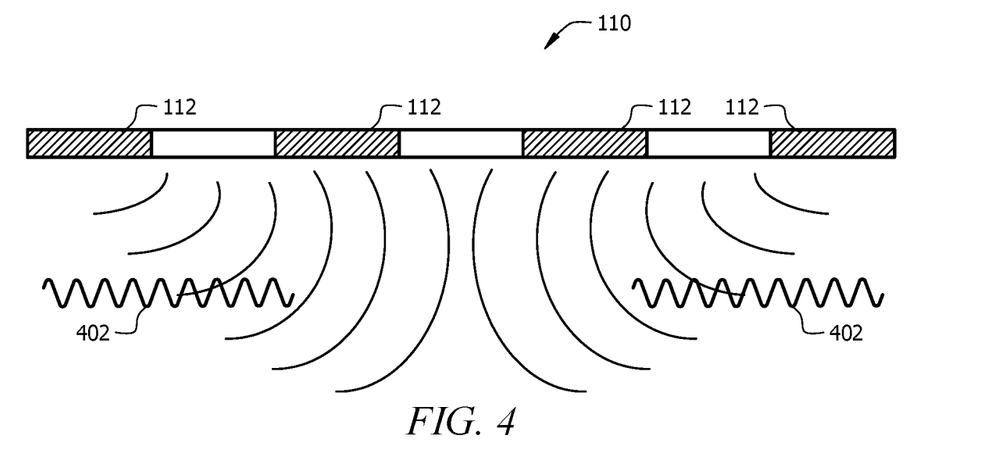
FIG. 4 illustrates an electrode array for use within an SCS according to an embodiment of the disclosure.

Referring to FIG. 4, in such embodiments, the phase of the electrical signals produced by the electrode contacts 112 may be configured to provide a phasic signal that penetrates deeper into the dorsal horn of the spinal cord, where visceral sensory processing occurs, without the discomfort associated with over stimulation of the more superficial dorsal horn where somatic sensation occurs. Treatment of visceral pain may be accomplished via the use of supra-physiologic frequencies that do not significantly stimulate the superficial dorsal horn but does allow the creation of one or more zones of induced current in the deeper dorsal horn via phased signal generation and/or the use of beat frequencies to create these deeper signal convergence zones that are in a physiologic stimulating frequency range.

The more superficial (or closer to the surface) portion of the dorsal horn, the sensory portion of the spinal cord, senses the arms and legs as well as the abdominal and chest wall. Slightly deeper in the dorsal horn are the nerves that sense internal organs, the viscera. The ability to stimulate the deeper dorsal horn without over-stimulating the more superficial dorsal horn (which is painful) would allow treatment of the internal organ pain, like pancreatitis and/or types of cancer pain. Current systems use a waveform 402 with no contrasting, interfering, differently phased or different frequency waveforms to exploit generation of non-linear electric fields.

Figure 5:
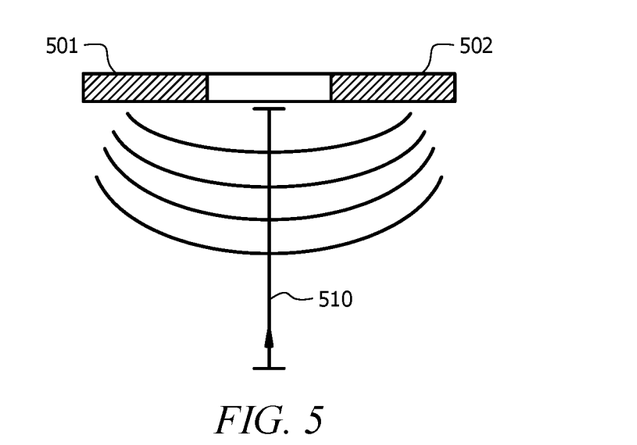
FIG. 5 illustrates an electrode array for use within an SCS according to an embodiment of the disclosure.

Referring to FIG. 5, at frequencies too high to stimulate the dorsal horn cells, adjustments to frequency, amplitude, current, phase, and additional beat frequencies may be used to induce zone of induced currents of lower frequency currents which physiologically would stimulate deeper tissues. The zone of induced current may be formed at an off axis distance 510 by adjusting the stimulation of a first electrode contact 501 and a second electrode contact 502 (which may be similar to the electrode contacts 112 described above). In one embodiment, the attributes of off axis distance 510 and frequency would determine induced current zones.

Figure 6A:
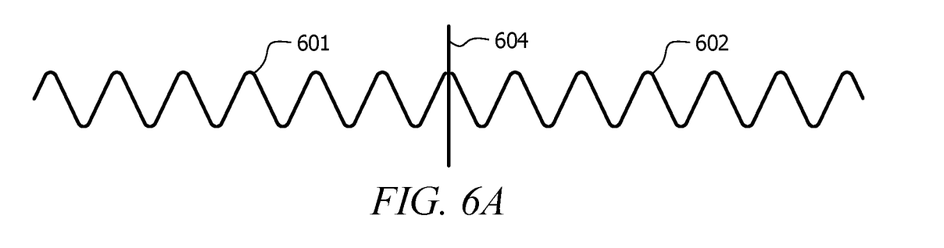
FIG. 6A illustrates interaction between two waveforms according to an embodiment of the disclosure.

FIG. 6A illustrates a near axis example, where the waveforms 601 and 602 meet at the same voltage (at point 604), so no current is induced. The waveforms 601 and 602 themselves are such high frequencies they do not stimulate the superficial dorsal horn neurons. In the embodiment shown in FIG. 6A, where the waveform voltages meet near the axis of the leads, the voltages are the same and no current is induced.

Figure 6B:
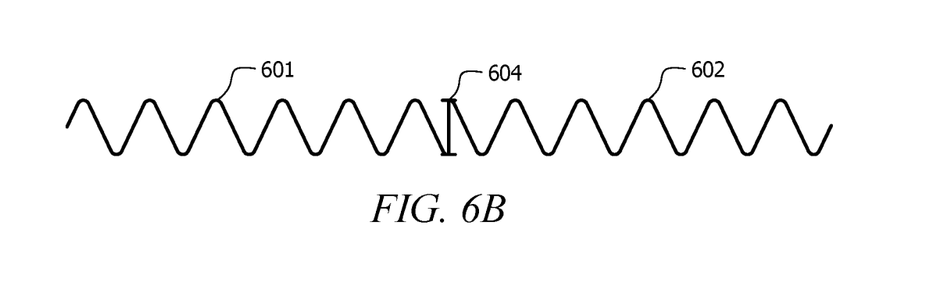
FIG. 6B illustrates interaction between two waveforms according to an embodiment of the disclosure.

Referring to FIG. 6B, by introducing a frequency differential (a "beat" frequency) of adjusting phasing, off-axis waveform phases may be affected to be different, meaning there is a voltage different or current induced where the waveforms 601 and 602 meet (at point 604). The off-axis waveforms 601 and 602 may stimulate deeper structures without over stimulating shallower neuronal structures, this technique is heavily dependent upon knowledge of the distance to the targeted stimulation zone. The difference in the voltage of these two waveforms 601 and 602 means a current is induced at this place in the spinal cord. A similar effect occurs with the use of beat frequencies, differential phasing in different leads and amplitude modulation of high frequencies to create zones of induced current with a flux similar in magnitude to current curvilinear stimulation fields.

In an embodiment both curvilinear and non-curvilinear modes of stimulation could be used simultaneously or switched at such a high rate as to appear physiologically as simultaneous to achieve relief for both somatic and visceral pain in patients suffering from both conditions. In some embodiments, it may be possible for the same system to use direct current stimulation from at least one electrode contact, and to use at least two electrode contacts to generate zone of induced current for stimulation of a portion of the patient's spinal cord. For example, when the spinal cord is positioned a first distance away from the lead (as described above), as measured by the sensor, direct current stimulation from one or more electrode contacts may be appropriate to stimulate a target area of the spinal cord. Then, if the spinal cord moves (with movement of the patient) to a second distance away from the lead, as measured by the sensor, stimulation may be accomplished by generating a zone of induced current using two electrode contacts (as described above), where possibly one of the two contacts is the same contact that generated the direct current stimulation. Alternatively, the electrode contacts may all be a part of an electrode array, where any of a number of electrode contacts may be used individually or together.

To treat certain types of pain, different electric field configurations may be needed. As an example, to treat angina the higher thoracic and lower cervical cord may be stimulated. Because the spinal cord itself is foreshortened so that the parenchyma of the cord does not correspond to the vertebral segment from which each spinal nerve exits, stimulation typically occurs above the actual vertebral segment associated with innervation of the target pain site. Similarly, to treat renal colic and/or pancreatitis, the middle to upper thoracic cord may be stimulated and to treat sources of pelvic pain, the lower thoracic spinal cord may be stimulated.

In an embodiment, the present disclosure comprises interferential therapy utilizing a multiplicity of medium to high frequency currents which may be passed simultaneously through the tissue of interest (e.g., spinal) where they are configured so that their paths cross and they literally interfere giving rise to an interference, interaction, induced or beat frequency. The exact frequency of the resultant beat frequency may be controlled by the input frequencies. An exemplary and non-limiting example would be the use of a first signal having a frequency of 4000 Hz and a companion signal having a frequency of 3900 Hz to result in a beat frequency of 100 Hz carried on a medium frequency 3950 Hz amplitude modulated current. The ability to treat visceral pain in this way would reduce the need for chronic opiate therapy and its attendant risks and avoid the associated problem of tolerance. In an embodiment, the present disclosure allows for phasic signals of sufficient intensity to provide electrical stimulation while avoiding discomfort in superficial tissues (such as skin or muscles).

Figure 7:
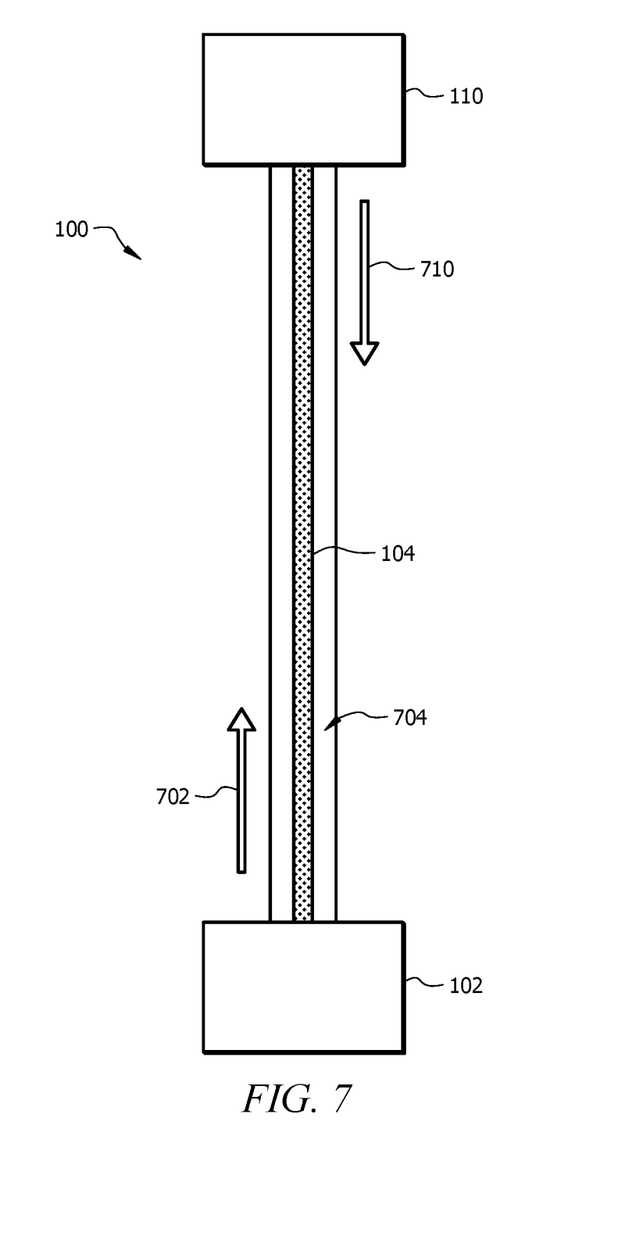
FIG. 7 illustrates communication between one or more elements of an SCS according to an embodiment of the disclosure.

All lead contacts and conductors disclosed herein may be electrically insulated by a suitable insulating material which is safe for implantation in the human body. Referring to FIG. 7, in some embodiments, an insulating material 704 surrounding the lead 104 (described above) may comprise optical communication properties, such as fiber optic materials. With newer fiber optic materials that are more flexible and tolerate mechanical cycling, communication between the stimulator generator and the distal leads is practical. Using the insulation as a fiber optic communication tool would enable improved communication between the generator 102 and the components at the distal end of the lead 104, such as the electrode array 110. The insulation material 704 may allow for communication from the generator to the electrode array to control the configuration of the electrode array, to augment the functionality of the system. For example, photons may travel in the direction indicated by arrow 702 from the generator 102 to the electrode array 110 (and/or other elements of the lead 104). The lead 104 and other elements, such as the electrode array 110, could also communicate directly with the generator 102. For example, photons may travel in the direction indicated by arrow 710 from the electrode array 110 (and/or other elements of the lead 104) to the generator 102. In one embodiment a magnetic sensing element in the distal lead array 110 could generate an optical signal to the IPG 102 to place the system into a safe mode to protect the patient from magnetically-induced currents associated with tissue damage. In another embodiment the IPG 102 could optically signal the distal lead array 110 to change lead configuration or augment lead function by activating additional capacitance elements or other features.

Additionally, the insulation material 704 may be magnetically insensitive, so that communication between the generator 102 and lead 104 can occur without being affected by a magnetic field. For example, an unanticipated magnetic field sensed by the generator and/or the distal leads, and the generator could automatically generate an optical signal to place the system in a "safe mode" to prevent an induced current from the exposure to the magnetic field.

The distal contact electrodes may have variable contact surface area as well as variable spacing between electrodes. The number of electrodes may be varied as well. Spinal cord stimulation generator systems transmit electrical current to the spinal cord via leads comprised of conductive elements. These conductive elements typically comprises a metallic alloy, such as platinum iridium alloys, and are subject to induced currents by dynamic magnetic fields such as those generated during a procedure such as magnetic resonance image (MRI) scanning. The currents induced by the conductive elements connecting the stimulator generator to the contacts positioned over the spinal cord presents risks of damaging adjacent tissues and the spinal cord. In an embodiment, a lead utilized in an SCS of the present disclosure is comprised of a material which does not generate an induced current in dynamic magnetic fields. Additionally, a material suitable for use in the present disclosure may be characterized by being resistant to deformation when subjected to a repetitive mechanical stress. In an embodiment, one or more leads of the present disclosure are prepared from and/or comprises conductive carbon fiber or nano-tubule conductive carbon fiber which in pure form has no magnetic moment. Without wishing to be limited by theory the use of a diamagnetic conductive material (e.g., carbon fiber) may significantly reduce the risk and the cost of risk mitigation measures for MRI-compatible or MRI-safe spinal cord stimulation systems. The systems of the present disclosure provide electromagnetically compatible implantable electronic medical devices which do not comprise the functioning of a device that induces a magnetic field.

In an embodiment, a SCS of the type disclosed herein is used in the treatment of neuropathic pain. In an alternative embodiment a SCS of the type disclosed herein is used to treat nociceptive pain. In an embodiment a SCS of the type disclosed herein is used in the treatment of failed back syndrome.

In some embodiments, the process for implanting or inserting a PACS as described above may comprise the use of an Intraoperative Programming Display System. Currently, stimulator systems are placed via 3-way verbal communication between the surgeon, the field support representative (or technician), and the patient. This trial and error technique is insensitive to specific flux through tissue, merely currents to achieve this flux.

Figure 8:
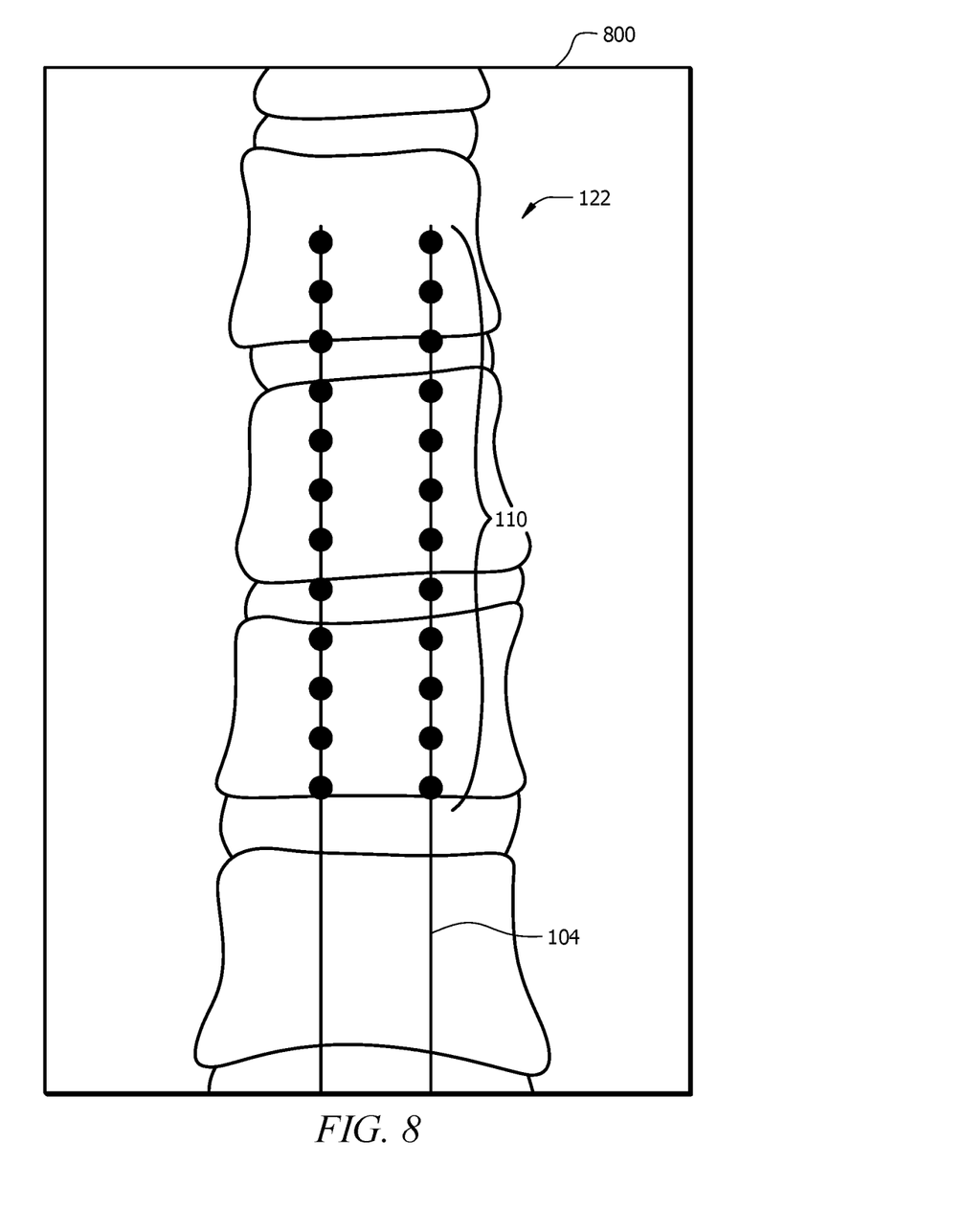
FIG. 8 illustrates a display for use when placing an SCS according to an embodiment of the disclosure.

Referring to FIG. 8, an integrated programming system comprising a display 800 may be configured to import images of an individual patient's stimulation target zone (as well as operating room (OR) images) and model the flux through these zones intraoperatively during programming for the surgeon to coordinate with the company rep and patient response. The ongoing, real-time OR image of lead placement would be imported into the system which would already have loaded into it selective preoperative imagery of the patient's spine and spinal cord in axial, coronal, and sagittal views. The ability to graphically overlay labels of each vertebral body level would assist in placement. As the rep adjusts the current levels and lead configuration, field lines color coded by current density (flux) would also appear. This could be done in anterior-posterior projection, coronal, axial, and sagittal views simultaneously. The display 800 may provide a model to the surgeon while working that illustrates where they are in the cord, how deep they're going, and the field density, where different colors may represent different field densities or levels of flux.

Currently, leads are placed under fluoroscopy, which only denotes the vertebral segment level of the leads. In the embodiments described here, a representative or technician may communicate with the patient while the surgeon places and adjusts the leads within the patient's spinal cord. The representative may cycle through different electrode configurations, and the display 800 may illustrate different characteristics of the electric field based on the current configuration. The display 800 may comprise imported images of the patient's anatomy, as well as real-time lead configuration information. The ability to generate this image in the operating room would include the ability to sense the distance of the dorsal surface of the spinal cord.

Embodiments of the disclosure include an electrotherapeutic modality comprising an MM compatible cardiac pacemaker. In an embodiment, a cardiac pacemaker of the present disclosure may be coupled to the heart by a pair of endocardial leads. A first lead is designated as a right atrial lead and includes a bipolar pair of electrodes at its distal end for making electrical contact with the right atrium in a suitable manner. A second lead is designated as a right ventricle lead and similarly includes a bipolar pair of electrodes at its distal end for making electrical contact with the right ventricle in a suitable manner. In an embodiment, a cardiac pacemaker lead system may have a single contact in the distal portion of the lead for each chamber, atrium or ventricle. In an embodiment, a cardiac pacemaker lead system may have a plurality contacts in the distal portion of the lead for each chamber, atrium or ventricle. In an embodiment, one or more leads of the present disclosure are prepared from and/or comprises conductive carbon fiber or nano-tubule conductive carbon fiber which in pure form has no magnetic moment. The cardiac pacemaker may further include without limitation a hermetic enclosure rendering the cardiac pacemaker fully implantable beneath the skin of a patient. Within the enclosure the cardiac pacemaker may include an atrial sense amplifier a ventricular sense amplifier, an analog to digital converter, and a pulse generator, a microprocessor, a memory and a telemetry stage.

Having described various devices and methods herein, exemplary embodiments or aspects can include, but are not limited to:

In a first embodiment, a spinal cord stimulator may comprise a pulse generator comprising electronic circuitry configured to generate output current; at least one lead in communication with the generator and configured to extend into the epidural space of a patient's spinal column; at least one electrode contact located proximate to a distal end of the at least one lead and configured to provide electric stimulation to a portion of a patient's spinal cord; and at least one sensor located along the at least one lead configured to determine a distance between the at least one lead and a surface of the patient's spinal cord, wherein the generator receives the determined distance, and wherein the generator is configured to adjust the stimulation provided by the at least one electrode contact based on the determined distance.

A second embodiment can include the spinal cord stimulator of the first embodiment, further comprising an electrode array comprising a plurality of electrode contacts located proximate to the distal end of the at least one lead.

A third embodiment can include the spinal cord stimulator of the second embodiment, wherein the electrode array is configured to produce a zone of induced current between a first electrode contact and a second electrode contact, and wherein the zone of induced current is located within the patient's spinal cord.

A fourth embodiment can include the spinal cord stimulator of the third embodiment, wherein the generator is configured to adjust the stimulation based on the determined distance by adjusting the location of the zone of induced current produced by the electrode array.

A fifth embodiment can include the spinal cord stimulator of any of the first through fourth embodiments, wherein the at least one sensor comprises an ultrasonic sensor.

A sixth embodiment can include the spinal cord stimulator of any of the first through fifth embodiments, wherein the at least one sensor comprises a piezoelectric element configured to generate an ultrasound signal; and a detector element configured to detect any reflected ultrasound signal.

A seventh embodiment can include the spinal cord stimulator of the sixth embodiment, wherein the reflected ultrasound signal is reflected from a dorsal surface of the patient's spinal cord.

An eighth embodiment can include the spinal cord stimulator of any of the first through seventh embodiments, wherein the at least one sensor is configured to detect the distance between the at least one lead and the surface of the patient's spinal cord periodically.

A ninth embodiment can include the spinal cord stimulator of any of the first through eighth embodiments, further comprising an insulation material surrounding the at least one lead.

A tenth embodiment can include the spinal cord stimulator of any of the first through ninth embodiments, further comprising a motion sensor configured to detect motion or movement by a patient, wherein the generator is configured to trigger the at least one sensor to determine the distance between the at least one lead and the surface of the patient's spinal cord based on the detected motion by the motion sensor.

In an eleventh embodiment, a method of electrotherapeutic modality may comprise placing one or more leads within the epidural space of a patient's spinal column; positioning the one or more leads proximate to a target stimulation area of a patient's spinal cord; stimulating at least one electrode contact located proximate to a distal end of the one or more leads by generating an output current by a generator in communication with the one or more leads; determining a distance, by a sensor, between the one or more leads and a surface of the patient's spinal cord; and adjusting a stimulation of the at least one electrode contact based on the determined distance.

A twelfth embodiment can include the method of the eleventh embodiment, further comprising detecting a change in the position of the patient's spinal cord with respect to the one or more leads, and activating the sensor for determining the distance between the one or more leads and the surface of the patient's spinal cord.

A thirteenth embodiment can include the method of the twelfth embodiment, further comprising detecting a patient's motion, and activating the sensor for determining the distance between the one or more leads and the dorsal surface of the patient's spinal cord.

A fourteenth embodiment can include the method of any of the eleventh through thirteenth embodiments, wherein stimulating at least one electrode contact further comprises stimulating a portion of the patient's spinal cord via current stimulation from the at least one electrode contact.

A fifteenth embodiment can include the method of any of the eleventh through fourteenth embodiments, wherein adjusting the stimulation of the at least one electrode contact comprises adjusting an intensity of a current stimulation from the at least one electrode contact.

A sixteenth embodiment can include the method of any of the eleventh through fifteenth embodiments, wherein stimulating at least one electrode contact comprises stimulating a first electrode contact; stimulating a second electrode contact; and creating a zone of induced current within the patient's spinal cord based on stimulating the first electrode contact and the second electrode contact.

A seventeenth embodiment can include the method of the sixteenth embodiment, wherein adjusting the stimulation of the at least one electrode contact comprises adjusting the stimulating of the first electrode and adjusting the stimulating of the second electrode, and wherein adjusting the stimulating of the first electrode and adjusting the stimulating of the second electrode changes a position of the zone of induced current created by the stimulating of the first electrode contact and the second electrode contact.

A eighteenth embodiment can include the method of any of the eleventh through seventeenth embodiments, wherein determining the distance, by the sensor, between the one or more leads and the surface of the patient's spinal cord comprises generating, by the sensor, an ultrasound signal; detecting, by the sensor, a reflected ultrasound signal, wherein the ultrasound signal is reflected by the surface of the patient's spinal cord; and analyzing the detected reflected ultrasound signal to determine a distance between the sensor and the surface of the spinal cord.

A nineteenth embodiment can include the method of any of the eleventh through eighteenth embodiments, wherein adjusting the stimulation of the at least one electrode contact comprises adjusting at least one of a pulse strength, a phase, a frequency, and a duration of the stimulation.

In a twentieth embodiment, a method of electrotherapeutic modality may comprise placing one or more leads within an epidural space of a patient's spinal column; positioning the one or more leads proximate to a target stimulation area of a patient's spinal cord; stimulating a first electrode contact located proximate to a distal end of the one or more leads by generating a first output current by a generator in communication with the one or more leads; stimulating a second electrode contact located proximate to a distal end of the one or more leads by generating a second output current by the generator in communication with the one or more leads; creating a zone of induced current causing stimulation based on stimulating the first electrode contact and the second electrode contact; determining a distance, by a sensor, between the one or more leads and a surface of the patient's spinal cord; and adjusting a position of the zone of induced current of stimulation based on the determined distance.

The invention claimed is:

1. A spinal cord stimulator comprising:
   a pulse generator comprising electronic circuitry configured to generate output current;
   at least one lead in communication with the generator and configured to extend into an epidural space of a spinal column of a patient, wherein the at least one lead comprises no magnetic moment;
   at least one electrode contact located proximate to a distal end of the at least one lead and configured to provide electric stimulation to a portion of a spinal cord of the patient; and
   at least one sensor located along the at least one lead configured to (i) emit an ultrasound signal, (ii) detect a reflected ultrasound signal, and (iii) send ultrasound information, wherein ultrasound information consists essentially of ultrasound signal information and reflected ultrasound signal information;
   a microcontroller, wherein the microcontroller is configured to receive the ultrasound information and determine a distance between the at least one lead and a surface of the spinal cord, wherein a calculation of a determined distance by the microcontroller consists essentially of using the ultrasound information, wherein the generator receives the determined distance, and wherein the generator is configured to dynamically adapt to alterations in a patient's postural position and adjust the stimulation provided by the at least one electrode contact based on the dynamically determined distance.

2. The spinal cord stimulator of claim 1, further comprising an electrode array comprising a plurality of electrode contacts located proximate to the distal end of the at least one lead.

3. The spinal cord stimulator of claim 2, wherein the electrode array is configured to produce a zone of induced current between a first electrode contact and a second electrode contact, and wherein the zone of induced current is located within the spinal column.

4. The spinal cord stimulator of claim 3, wherein the generator is configured to adjust the stimulation based on the determined distance by adjusting the location of the zone of induced current produced by the electrode array.

5. The spinal cord stimulator of claim 1, wherein the at least one sensor comprises a piezoelectric element configured to generate the ultrasound signal; and a detector element configured to detect the reflected ultrasound signal.

6. The spinal cord stimulator of claim 5, wherein the reflected ultrasound signal is reflected from a dorsal surface of the spinal cord.

7. The spinal cord stimulator of claim 1, wherein the at least one sensor is configured to detect signals related to the distance between the at least one lead and the surface of the spinal cord periodically.

8. The spinal cord stimulator of claim 1, further comprising an insulation material surrounding the at least one lead.

9. The spinal cord stimulator of claim 1, further comprising a motion sensor configured to detect motion or movement by a patient, wherein the generator is configured to trigger the at least one sensor to send ultrasound information to the microcontroller to determine the distance between the at least one lead and the surface of the spinal cord based on the detected motion by the motion sensor.

10. A method of electrotherapeutic modality, comprising:
    placing one or more leads within an epidural space of a spinal column of a patient, wherein the one or more leads comprise no magnetic moment;
    positioning the one or more leads proximate to a target stimulation area of a spinal cord of the patient;
    stimulating at least one electrode contact located proximate to a distal end of the one or more leads by generating an output current by a generator in communication with the one or more leads;
    emitting, by the sensor, an ultrasound signal;
    detecting, by the sensor, a reflected ultrasound signal;
    sending ultrasound information, by the sensor, to a microcontroller, wherein ultrasound information consists essentially of ultrasound signal information and reflected ultrasound signal information;
    determining, by a microcontroller, a distance between the one or more leads and a surface of the spinal cord, wherein a calculation of a determined distance by the microcontroller consists essentially of using the ultrasound information;
    dynamically adapting, by the microcontroller, to alterations in a patient's postural position; and
    dynamically adjusting a stimulation of the at least one electrode contact based on the determined distance.

11. The method of claim 10, further comprising detecting a change in the position of the spinal cord with respect to the one or more leads, and activating the sensor for collecting information concerning the distance between the one or more leads and the surface of the spinal cord.

12. The method of claim 11, further comprising detecting a motion of the patient, and activating the sensor for collecting information concerning the distance between the one or more leads and the dorsal surface of the spinal cord.

13. The method of claim 10, wherein stimulating at least one electrode contact further comprises stimulating a portion of the spinal cord via current stimulation from the at least one electrode contact.

14. The method of claim 10, wherein adjusting the stimulation of the at least one electrode contact comprises adjusting an intensity of a current stimulation from the at least one electrode contact.

15. The method of claim 10, wherein stimulating at least one electrode contact comprises:
    stimulating a first electrode contact;
    stimulating a second electrode contact; and
    creating a zone of induced current within the spinal cord based on stimulating the first electrode contact and the second electrode contact.

16. The method of claim 15, wherein adjusting the stimulation of the at least one electrode contact comprises adjusting the stimulating of the first electrode and adjusting the stimulating of the second electrode, and wherein adjusting the stimulating of the first electrode and adjusting the stimulating of the second electrode changes a position of the zone of induced current created by the stimulating of the first electrode contact and the second electrode contact.

17. The method of claim 10, wherein adjusting the stimulation of the at least one electrode contact comprises adjusting at least one of a pulse strength, a phase, a frequency, and a duration of the stimulation.

18. A method of electrotherapeutic modality, comprising:
placing one or more leads within an epidural space of a spinal column of a patient, wherein the one or more leads comprise no magnetic moment;
positioning the one or more leads proximate to a target stimulation area of a spinal cord of the patient;
stimulating a first electrode contact located proximate to a distal end of the one or more leads by generating a first output current by a generator in communication with the one or more leads;
stimulating a second electrode contact located proximate to a distal end of the one or more leads by generating a second output current by the generator in communication with the one or more leads;
creating a zone of induced current causing stimulation based on stimulating the first electrode contact and the second electrode contact;
collecting ultrasound information, by a sensor, wherein the ultrasound information concerns a distance between the one or more leads and a surface of the spinal cord;
sending the ultrasound information, by a sensor, to a microcontroller;
determining a distance, by a microcontroller, between the one or more leads and a surface of the spinal cord, wherein a calculation of a determined distance by the microcontroller consists essentially of using the ultrasound information;
dynamically adapting, by the microcontroller, to alterations in a patient's postural position; and
dynamically adjusting a position of the zone of induced current causing stimulation based on the determined distance.

* * * * *